United States Patent [19]

Ishihara et al.

[11] Patent Number: 4,469,593
[45] Date of Patent: Sep. 4, 1984

[54] BLOOD PURIFICATION APPARATUS

[75] Inventors: Toshikazu Ishihara; Tomoyuki Kitano, both of Aichi, Japan; Kenji Maeda, Yatagawa Park House C, 10-7, Daiko-cho, Higashi-ku, Nagoya, Aichi, Japan; Toru Shinzato, Aichi, Japan

[73] Assignees: Kabushiki Kaisha Toyota Chuo Kenkyusho; Kenji Maeda, both of Aichi, Japan

[21] Appl. No.: 473,574

[22] Filed: Mar. 9, 1983

[30] Foreign Application Priority Data

Mar. 10, 1982 [JP] Japan ................................. 57-37457
Dec. 21, 1982 [JP] Japan ................................. 57-224743

[51] Int. Cl.³ ............................................. B01D 13/00
[52] U.S. Cl. .................................. 210/96.2; 210/104; 210/321.1
[58] Field of Search .............................. 210/739–748, 210/96.2, 104, 87, 188, 321.1

[56] References Cited

U.S. PATENT DOCUMENTS

| | | | |
|---|---|---|---|
| 1,124,600 | 1/1915 | Franklin | 210/748 |
| 4,113,614 | 9/1978 | Rollo | 210/87 |
| 4,153,554 | 5/1979 | Heide et al. | 210/96.2 |
| 4,209,391 | 6/1980 | Lipps | 210/188 |
| 4,347,110 | 8/1982 | Joyce | 210/748 |

Primary Examiner—John Adee
Attorney, Agent, or Firm—Koda and Androlia

[57] ABSTRACT

A blood purification apparatus includes an extracorporeal circulation system, a blood purifier provided in the system for purifying blood by dialysis or filtration through a semipermeable membrane, a circulation blood volume measuring instrument for measuring changes in a circulating blood volume within a patient's body, a control section comprising a memory for storing a program for a pattern of changes in the circulating blood volume during blood purification, the program being matched to the condition of a patient, and a regulator connected to the extracorporeal circulation system and the control section, for controlling the circulating blood volume, the regulator being controlled by the control section on the basis of the circulating blood volume measured during blood purification and the programmed amount. In this apparatus, optimum blood purification is carried out while maintaining the circulating blood volume at a prescribed level.

25 Claims, 15 Drawing Figures

BLOOD PURIFICATION APPARATUS

DETAILED DESCRIPTION OF THE INVENTION

1. Field of the Invention

This invention relates to an apparatus for purifying blood by dialysis and/or filtration, using a semipermeable membrane and more particularly to an improved blood purification apparatus enabling appropriate automatic control of changes in circulating blood volume in the patient's body.

2. Field of the Invention

In recent years patients who have lost the ability to keep their blood free of waste products because of renal failure or other disorders have been treated using a blood purification apparatus which purifies blood removed from the patient's body by dialysis and/or filtration using a semipermeable membrane and then returns the purified blood to the patient.

It is well known that in this type of apparatus water must be removed with the waste products by ultrafiltration and it is necessary to maintain the water removal rate appropriately. More specifically, rapid and excessive water removal causes a rapid and excessive decrease in the circulating blood volume within the patient's body and consequently results in symptomatic hypotension or shock.

On the other hand, when the water removal is too slow, a long time is required for blood purification and, if the amount of removal should be insufficient, there is the danger of the occurrence of hypertension or heart failure.

Therefore, in conventional apparatuses the total amount of water removal has been maintained at an appropriate level in the case of hemodialysis by maintaining the ultrafiltration rate at a fixed level during dialysis or by determining the ultrafiltration rate in accordance with a water removal program set empirically beforehand at the start of dialysis.

Unfortunately, however, it has become clear in recent years that the control of ultrafiltration rate in the conventional mode is not enough to maintain patients in excellent condition during blood purification. This is because most discomfort during blood purification results from excessive decrease of the circulating blood volume within the patient's body, which is related not only to the water removal rate but also to water transfer rate through the capillary walls. Therefore, it is obviously difficult to appropriately control the circulating blood volume within the patient's body merely by controlling the ultrafiltration rate as has been the conventional practice up to now.

Another conventional method for carrying out appropriate control during blood purification involves measurement of the electrical impedance of the blood and carrying out control on the basis of the measured value to prevent excessive water removal from the patient's body during blood purification. For example, changes in the electrical impedance of the blood in the extracorporeal circulation system are measured on the arterial blood line or on both the arterial and venous blood lines of the hemodialyzer, and on the basis of the measured changes in impedance, control is carried out to reduce the operation rate of the hemodialyzer to the present level or to inject a plasma product into the blood circulatory path.

With these conventional apparatuses, however, it has been difficult to appropriately control the circulating blood volume in the patient's body since the electrical resistivity of blood not only depends on the chemical condition of blood and water content but is also greatly affected by other factors such as blood temperature and flow rate and particularly by erythrocyte orientation and axial accumulation associated with the flow of blood. As for the conventional apparatuses, as they do not take all of these various factors into consideration, they are not capable of accurately measuring changes in water content and therefore cannot carry out the required control properly. A specific problem in this connection has been that in the conventional method the resistivity of the blood is measured by passing a current between electrodes provided at locations separated from each other in the flow direction of the blood. In this case, however, the measured value obtained for flowing blood is much smaller than that obtained for the same blood at rest, making it difficult to carry out measurement accurately. For example, when the resistivity of blood having a hematocrit of 36% is measured using a measurement frequency of 10 KHz, the value obtained at a shear rate of 100 $S^{-1}$ is 12% less than that for the same blood at rest.

The conventional apparatuses moreover have a fundamental problem in that they do not carry out feedback control but merely carry out control of the purification rate and other factors on an emergency basis when one of the factors being monitored, for example the change in electrical resistivity of the blood, has reached a prescribed dangerous level. Thus, like earlier apparatuses with no control capability, they merely carry out purification under predetermined fixed conditions and are incapable of properly controlling water removal in a comprehensive and continuous manner.

In order to carry out appropriate blood purification by hemofiltration, another known method of blood purification, it is necessary, at the time of removing large amounts of ultrafiltrate from the blood together with undesirable waste products, to supplement the blood with a replacement liquid in an amount equal to or slightly less than the amount of ultrafiltrate so as to prevent a sudden drop in the circulating blood volume within the patient's body.

For this purpose it has been proposed to carry out control in the hemofiltration device with respect to a predetermined difference in weight or volume between the amount of filtrate and the amount of supplied liquid so as to maintain a balance between the two each time. This method is disadvantageous, however, because it requires an elaborate and bulky apparatus and because it is incapable of appropriately controlling the circulating blood volume within the patient's body since, as explained earlier, the circulating blood volume in the patient's body is not determined solely by the amount of water removed (the difference between the amount of filtrate and the amount of replacement liquid).

Because of these shortcomings of conventional apparatuses, there has been strong interest in the development and reduction to practice of a blood purification apparatus capable of automatically controlling the rate at which water is removed from the patient so as to maintain the circulating blood volume within the patient's body at an appropriate level each time during blood purification. Moreover, it has in recent years been found that control of water removal rate alone is not sufficient.

This is because changes (decreases) in the circulating blood volume within the patient's body are equal to the difference between (1) the amount of water moving from interstitial space into the blood vessels associated with variations in body fluid distribution resulting from the adjustment to differences in effective osmotic pressure and in mechanical pressure within the body, namely the amount of water transferred from interstitial space into the blood vessels and the amount of water transferred from intracellular space into interstitial space (the transfer of water being possible in either direction, that from the interstitial space into the blood vessels will be referred to as positive) and (2) the amount of water removed from the blood outside the body during blood purification.

If in order to rapidly remove the aforementioned solutes accumulated within the body there is used a replacement fluid in the case of hemofiltration or a dialysate in the case of hemodialysis which is completely free of the various components accumulated within the body or which contains them only in low concentrations, the osmotic pressure of the extracellular fluid will drop, causing water transfer from interstitial space into intracellular space and a consequent decrease in water transfer from interstitial space into the blood vessels and making it necessary to lower the water removal rate so as to maintain the circulating blood volume at the proper level. If, on the other hand, to avoid this situation a solution with a high osmotic pressure is used as the replacement fluid or dialysate, there is the danger of causing the accumulation of these solutes within the body.

Consequently, in order to carry out blood purification without excessively reducing the circulating blood volume within the patient's body but while removing a proper amount of water and the various solutes, it is necessary not only to maintain the water removal rate at an appropriate level but also to maintain a proper distribution of the body fluids, particularly the blood plasma and the intracellular and interstitial fluids. For this it is necessary to maintain the osmotic pressure of the patient's extracellular fluid including plasma at an appropriate level during the blood purification operation, which is to say that the concentration of the various solutes within the extracellular fluid must be maintained at an appropriate level. And, since the concentration of the solutes in the extracellular fluid is affected by the concentration of the solute in the replacement fluid or dialysate, it is necessary to appropriately control the solute concentration in the replacement fluid or dialysate in order to maintain the proper distribution of body fluids.

However, as the appropriate solute concentration of the replacement fluid or dialysate varies with the desired osmotic pressure of the body fluids and with conditions of the particular patient, the conventional apparatuses have been unable to determine the appropriate solute concentration of the replacement fluid or dialysate so that, as a result, it has as a practical matter been difficult to carry out blood purification in a manner best suited to each individual patient.

OBJECT OF THE INVENTION

One object of the present invention is to provide a blood purification apparatus which overcomes the problems discussed above with respect to the prior art and more specifically to provide a blood purification apparatus for continuously purifying the extracorporeally circulating blood of a patient, which is capable of stably carrying out efficient water removal from the body while maintaining the circulating blood volume within the patient's body at an appropriate level.

Another object of the present invention is to provide a blood purification apparatus for continuously purifying the extracorporeally circulating blood of a patient by dialysis or hemofiltration using a semipermeable membrane, which is capable of stably carrying out well-balanced removal of waste products from the body while maintaining the circulating blood volume within the patient's body at an appropriate level.

DESCRIPTION OF PREFERRED EMBODIMENTS

Embodiments of this invention will now be explained in detail with reference to the drawings.

Figure 1:
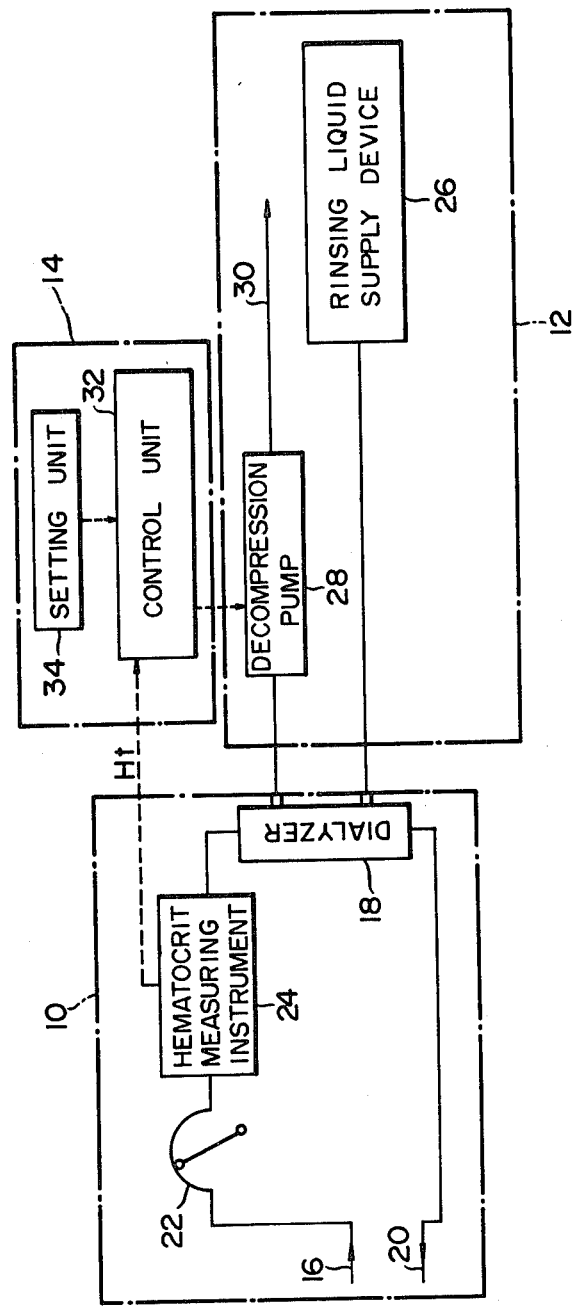
FIG. 1 is a block diagram of the first embodiment of the blood purification apparatus in accordance with this invention.

First embodiment:

FIG. 1 shows the basic structure of the first embodiment of the invention, which is used for hemodialysis. The apparatus includes an extracorporeal circulation system 10 through which blood removed from the patient's body is circulated, a dialysate section 12 for supplying dialysate to the extracorporeal circulation system 10 and a control section 14 for controlling a decompression pump 28 in accordance with the hematocrit detected in the extracorporeal circulation system 10.

In the extracorporeal circulation system 10, blood from the patient is fed via an arterial blood line 16 to a dialyzer 18 which purifies the blood by dialysis and ultrafiltration in cooperation with the dialysate supplying section 12 whereafter the purified blood returns to the patient via a venous blood line 20. During this process the blood is circulated by a circulation pump 22.

In order to carry out optimum water removal in a generally known dialyzer such as that described above, the present invention provides a hematocrit measuring instrument 24 in the extracorporeal circulation system 10. This hematocrit measuring device 24 continuously measures the electrical resistance of the blood to obtain the blood hematocrit and the water removal is appropriately controlled to maintain the circulating blood volume within the patient's body, which amount is inversely proportional to the hematocrit, in conformity with a preset program.

The dialysate supplying section 12 associated with the dialyzer 18 is provided with a known dialysate supplying device 26 which supplies dialysate to the dialyzer 18. The dialyzer 18 is also connected to a decompression pump 28 which constitutes a a regulator for regulating the total body fluid volume change and acts as a regulator for the circulating blood volume within the patient's body. The decompression pump 28 applies a transmembrane pressure to the semipermeable membrane of the dialyzer 18 by reducing the pressure on the dialysate side, causing ultrafiltration from the blood side into the dialysate side through the semipermeable membrane. In this first embodiment of the invention the transmembrane pressure generated by the decompression pump 28 is controlled by a control section 14 on the basis of the aforesaid hematocrit value, thus making it possible to appropriately control the ultrafiltration to the desired rate for each individual patient and to carry out optimum water removal without danger of causing complications in the patient during the blood purification operation.

The control section 14 consists of a control unit 32 for controlling the decompression pump 28 on the basis of the measured value transmitted from the hematocrit measuring instrument 24 and on the basis of a preset program, and a setting unit 34 for storing a program corresponding to the desired hematocrit variation pattern for the particular patient as determined from his medical record.

Figure 2:
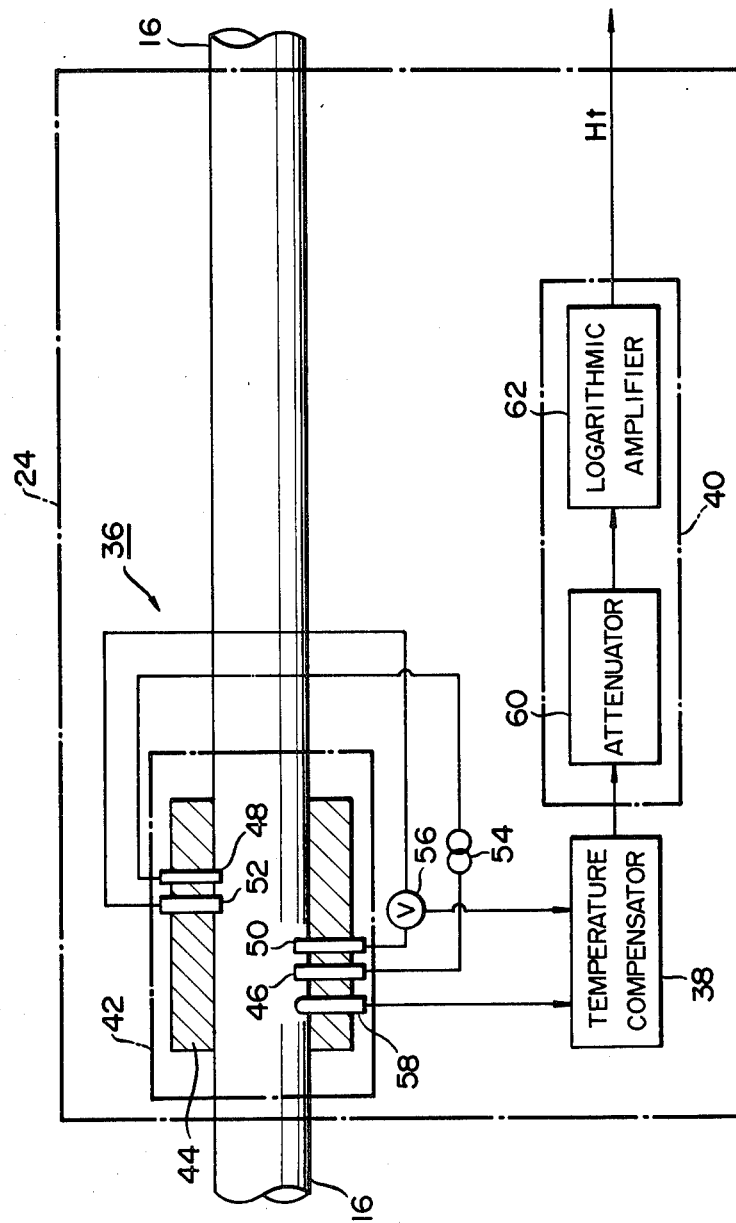
FIG. 2 is an explanatory view of the hematocrit measuring instrument used in the embodiment of FIG. 1.

The structure of the hematocrit measuring instrument is shown in detail in FIG. 2. As shown, the instrument comprises a resistivity measurement device 36 which measures the electrical resistivity of the blood entering via the inlet pipe 16, a temperature compensator 38 for compensating the measured resistivity for temperature, and an arithmetic circuit 40. The resistivity measurement device 36 has a measurement cell 42 connected to and communicating with the inlet pipe 16. The cell 42 measures electrical resistivity by the four-electrode method. In this embodiment, the electrodes are disposed in a special way in order to eliminate the effect of blood flow on the measurement. More specifically, an insulative pipe 44 is provided with a pair of current electrodes 46, 48 and a pair of voltage electrodes 50, 52, with the current electrodes 46, 48 being located at symmetrically opposite positions with respect to the axis of the insulative pipe 44 and being separated from one another by a desired distance in the direction of said axis, and with the voltage electrodes 50, 52 being provided inwardly of and parallel to the respective current electrodes 46, 48. As a result of this structure the resistivity of the blood is measured obliquely to the direction of blood flow. Measurement current is supplied between the current electrodes 46, 48 from a constant AC current source 54 and the resistivity of the blood is measured in terms of the voltage appearing across the voltage electrodes 50, 52. A voltmeter 56 is provided between the voltage electrodes 50, 52 to monitor this voltage and the output therefrom is forwarded to the temperature compensator 38.

In order to compensate for blood temperature, a thermistor for measuring temperature is provided in the insulative pipe 44 and the output terminal thereof is connected to the temperature compensator 38.

By the employment of a resistivity measuring device 36 having the above described structure it is possible to eliminate the effect of blood flow on the measured value. Blood consists of a corpuscular component (blood cells) and a non-corpuscular component (plasma) and, from the viewpoint of electrical properties, for the frequency range of 1 KHz to 1 MHz, can be considered to constitute a non-uniform system consisting of red cells with poor conductivity suspended in plasma with good conductivity. As red cells are biconcave disks, they orient themselves in the flow direction when blood flows in a tube and, as a result, the electrical resistivity of flowing blood depends on the direction of the applied electrical field. At a shear rate of 300 $S^{-1}$ or less, the electrical resistivity in the direction of flow decreases and that perpendicular to the direction of flow increases, making it difficult to determine the hematocrit accurately. Therefore, in this embodiment, the electrodes are positioned obliquely with respect to the direction of blood flow as described above. This enables measurement of the electrical resistivity in a direction that includes both a component in the direction of flow and in the direction perpendicular thereto so that even if electrical anisotropy has arisen in the blood due to its flow, it will still be possible to obtain the same measured value for the resistivity as would be obtained were the blood at rest since the effect of the anisotropy is canceled out. In this embodiment, with a view to assuring the safety of the patient and avoiding the effect of polarization, a current of 25 KHz and 30 $\mu$A rms is supplied from the constant AC current source 54, and, moreover, the voltmeter 56 converts the AC voltage to a DC voltage which it forwards to the temperature compensator 38.

In accordance with this arrangement, the electrical resistivity value obtained from the resistivity measurement device 36 is compensated for temperature by the temperature compensator 38 according to the resistance of the thermistor 58. Taking into consideration that in the vicinity of body temperature the electrical resistivity of blood decreases about 2% per 1° C. increase in temperature, the temperature compensation is carried out so as to convert the measured resistivity to that at 37° C.

Next, the temperature-compensated resistivity value is forwarded to the arithmetic circuit 40 where it is used to calculate the hematocrit. The relationship between the resistivity $\rho_b$ ($\Omega$ cm) of blood in the vicinity of 25 KHz and the hematocrit Ht according to the centrifugation method can be expressed as:

$$\rho_b = K_2 \, e^{\frac{1}{K1} Ht} \tag{1}$$

As, however, $K_1 \approx 47$ and $K_2 \approx 54$, the hematocrit Ht can be obtained as follows:

$$Ht = K_1 \ln \frac{\rho_b}{K_2} \qquad (2)$$

The arithmetic circuit 40 is provided with an attenuator 60 and a logarithmic amplifier 62 for calculating Ht in accordance with the formula (2).

Figure 3:
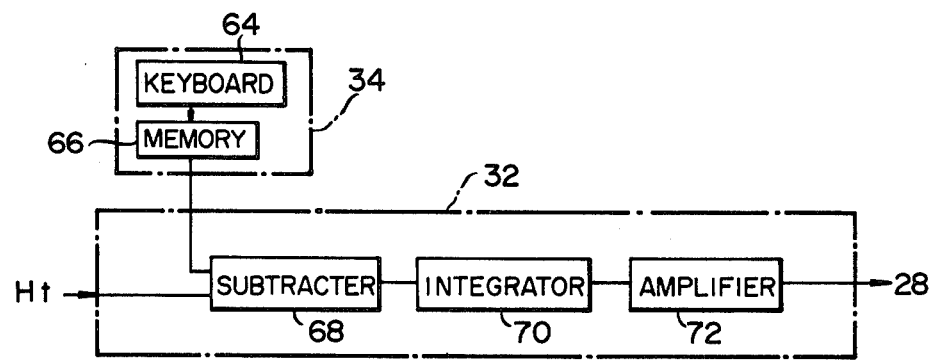
FIG. 3 is a block diagram of the control section used in the embodiment of FIG. 1.

It is a feature of this invention that the hematocrit calculated from the electrical resistivity of the blood in this way is used by the control section 14 to control the circulating blood volume in the patient's body. A preferred embodiment of the control section 14 is shown in FIG. 3.

In this embodiment the setting unit 34 stores the information obtained from the patient's medical records on the preferable pattern of variation in the circulating blood volume in the patient's body during dialysis as the pattern of hematocrit variation. It thus includes a keyboard 64 for imputting the hematocrit pattern program and a memory for storing information on the circulating blood volume in the patient's body, namely in this embodiment, hematocrit memory 66.

The control unit 32 is arranged to control the decompression pump 28 of the dialysate section 12 on the basis of the program stored in the hematocrit memory 66 and the measured value from the hematocrit measuring instrument 24. It therefore comprises a subtracter 68 for obtaining the difference between the hematocrit value according to the program stored in the hematocrit memory 66 and the measured hematocrit Ht obtained from the hematocrit measuring instrument 24 during dialysis, an integrator 70 for integrating this difference and producing a control signal, and an amplifier 72 for power-amplifying the signal from the integrator 70 and applying it to the decompression pump 28 as driving power.

In this invention, in the case where the hematocrit Ht is smaller than the value set by the program, the driving power supplied to the pump 28 is gradually increased and, on the contrary, when the hematocrit Ht is larger than the set value, the driving power supplied to the pump 28 is gradually decreased.

The operation of the first embodiment of the invention constructed as described above will now be explained in the following.

Prior to the start of hemodialysis, there is loaded in setting unit 34 a program reflecting the optimum pattern of hematocrit variation for the patient prepared on the basis of the weight gain from the preceding dialysis, his blood pressure and other aspects of his medical record. Following this, hemodialysis is conducted in the known manner.

In the present invention, the hematocrit is continuously measured during hemodialysis and, using the measured value, the control section 14 controls water removal in accordance with the aforementioned program.

In the course of hemodialysis, a desired level of ultrafiltration is generally carried out under the mechanical pressure generated by decompression pump 28 and osmotic pressure across the semipermeable membrane of the dialyzer 18. In other words, by maintaining the pressure on the dialysate side at a lower level, there is ultrafiltration from the blood side to the dialysate side through the semipermeable membrane. At this time, the ultrafiltrate per unit time is not equal to the water movement from interstitial space into the blood vessels through the capillary wall and this results in changes in the circulating blood volume within the patient's body during hemodialysis. Normally, about 1–3 l of water is removed totally during a single hemodialysis (4–6 hours) from the body. And uncontrolled water removal rate often causes an excessive decrease in circulating blood volume within the patient's body. It is a feature of this invention that in the course of hemodialysis circulating blood volume within the patient's body is controlled so as to be constantly maintained at a predetermined programmed value. To accomplish this, attention has been given to the fact that the total volume of the blood cells remains constant during hemodialysis (since they cannot pass through the semipermeable membrane) so that the circulating blood volume within the patient's body is inversely proportional to the hematocrit value. Therefore, the circulating blood volume in the patient's body can be maintained constant by controlling the decompression pump 28 so as to maintain the hematocrit, as measured, at the desired programmed value.

Therefore, in the first embodiment, when ultrafiltration proceeds rapidly and the circulatory blood volume drops quickly, since at this time the hematocrit will rise above the programmed value, the ultrafiltration pressure applied by the decompression pump 28 is reduced to prevent decrease in the circulatory blood volume. A similar type of control is also applied in the reverse case. As a consequence, by carrying out control in accordance with a predetermined pattern in this way it becomes possible to carry out water removal in a manner well suited to the patient's condition.

Figure 4:
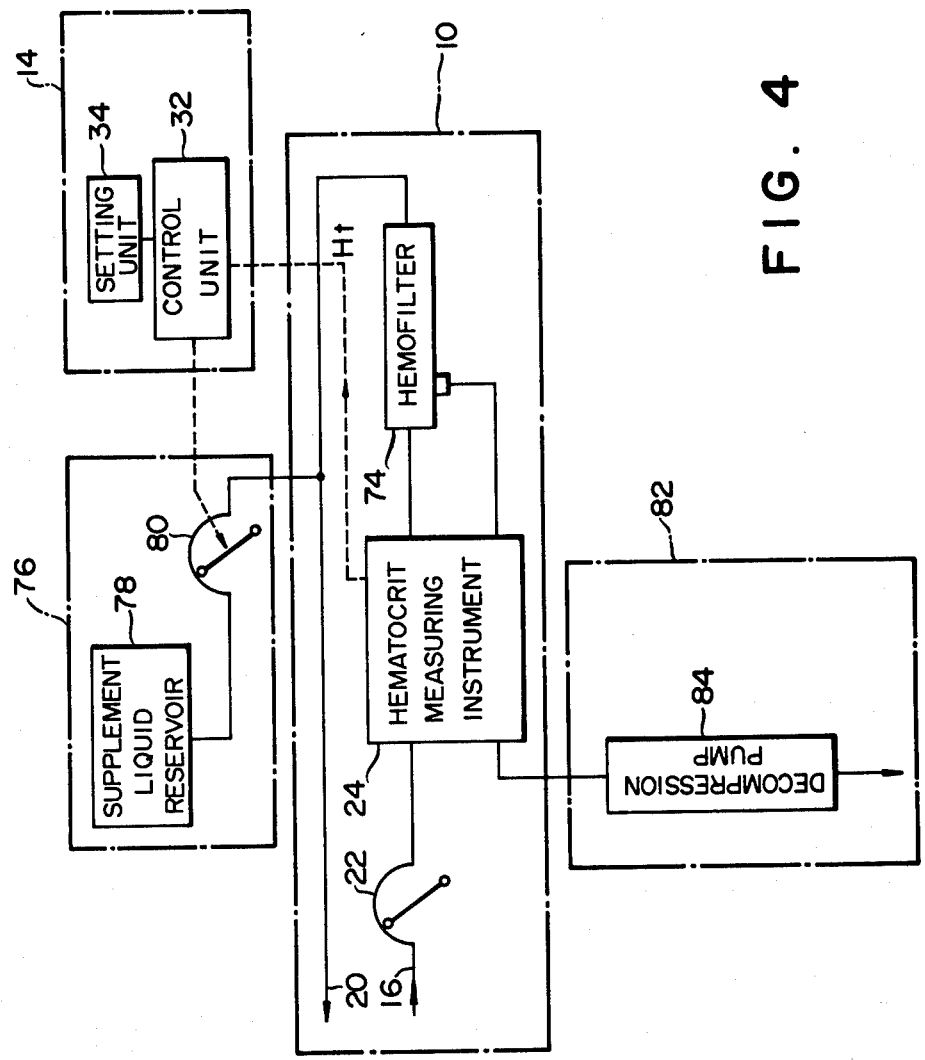
FIG. 4 is a block diagram of the second embodiment of the blood purification apparatus in accordance with this invention.

Second embodiment:

FIG. 4 shows a second embodiment of the blood purification apparatus according to this invention. Parts identical with those of the first embodiment are indicated by like reference numerals and explanation thereof is omitted.

Hemofiltration is carried out by a hemofilter 74 provided in the extracorporeal circulation system 10 and a decompression pump 84 provided in a waste fluid section 82. During this hemofiltration, replacement fluid is supplied to the extracorporeal circulation system 10 from a replacement fluid section 76. The purified blood is returned to the patient. For this purpose, the present embodiment is provided with a waste fluid section 82 for handling the waste fluid filtered from the blood by the hemofilter 74 in the extracorporeal circulation system 10, and the decompression pump 84 provided in the waste fluid section 82 applies negative pressure to the semipermeable membrane provided in the hemofilter 74 to carry out ultrafiltration.

The replacement fluid section 76 comprises a replacement fluid supply device 78 and a feed pump 80 for supplying replacement fluid to the extracorporeal circulation system 10. In this embodiment, the feed pump 80 of the replacement fluid section 76 constitutes a regulator for regulating the total body fluid volume change, i.e. a regulator for controlling the circulating blood volume in the patient's body. More specifically, the operating speed (rpm) of the feed pump 80 is controlled by a control signal from the control section 14 so as to regulate the amount of replacement fluid supplied to the extracorporeal circulation system 10 and thus to control circulating blood volume within the patient's body to the desired level.

In this embodiment, the hematocrit of the blood in the arterial blood line is measured and the measured value is used to control the replacement fluid section 76 which regulates the circulating blood volume in the patient's body. In this embodiment, since a large quantity of replacement fluid having a different electrolytic concentration from the extracellular fluid is injected into the patient's body from the replacement fluid section 76, a change occurs in the electrolytic concentration and electrical resistivity of the blood plasma. Under these circumstances, a hematocrit Ht calculated from only the electrical resistivity in accordance with formula (2) will involve an element of error. Therefore, in this embodiment, the hematocrit Ht is calculated from both the electrical resistivity $\rho_b$ of the blood and the electrical resistivity $\rho_p$ of the waste filtrate liquid which constitutes one part of the plasma. For this purpose, the waste fluid from the hemofilter 74 is supplied to the hematocrit measuring instrument 24.

Figure 5:
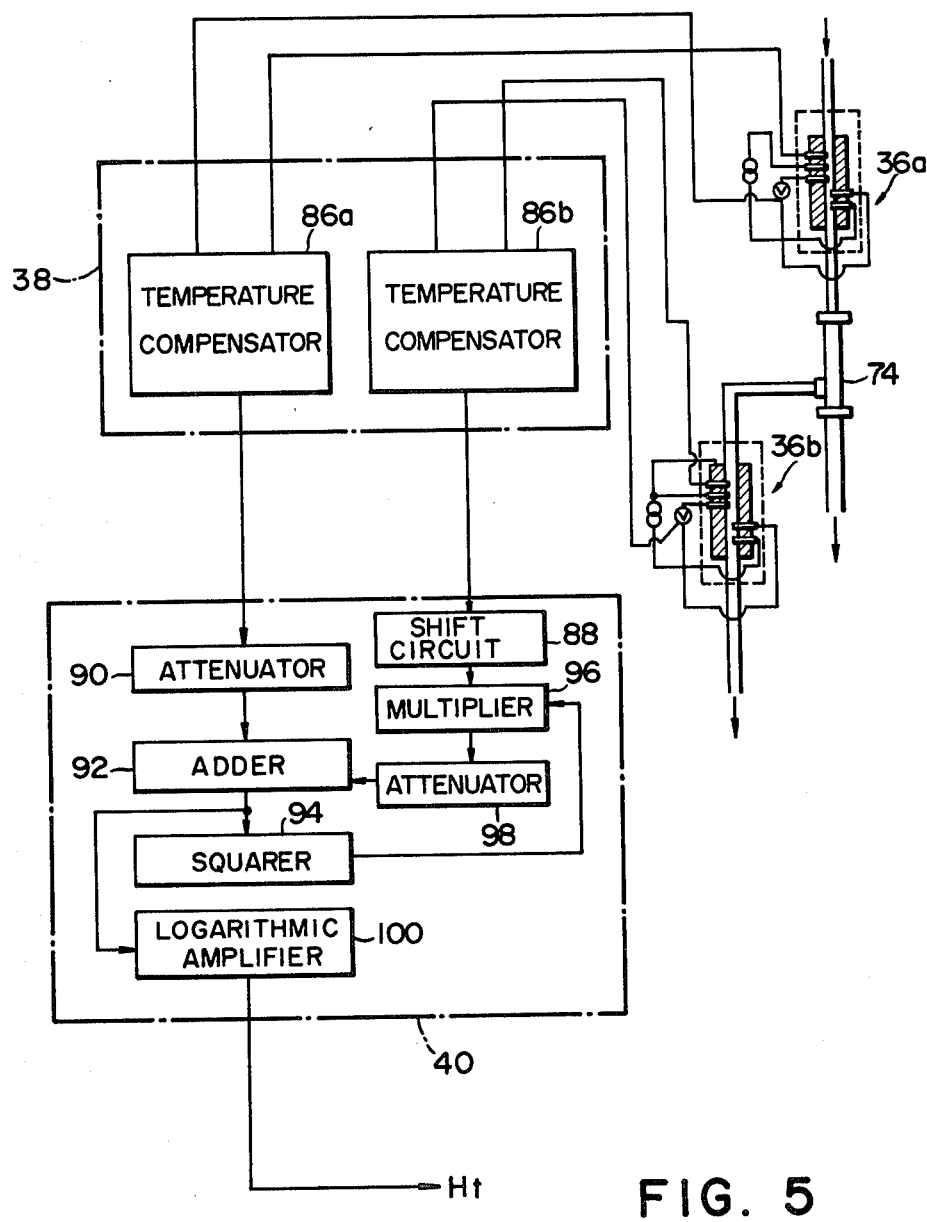
FIG. 5 is an explanatory view of the hematocrit measuring instrument used in the embodiment of FIG. 4.

The structure of the hematocrit measuring instrument 24 of this second embodiment is shown in FIG. 5.

As shown in FIG. 5, resistivity measurement devices 36a and 36b are provided on the arterial blood line and one on the ultrafiltrate discharge line from the hemofilter 74 respectively. These resistivity measurement devices are of the same structure as the resistivity measurement device 36 shown in FIG. 2. The electrical resistivity measurements from these devices 36a, 36b are forwarded to temperature compensators 86a, 86b where they are converted to the corresponding values for the blood at 37° C. and the compensated values are forwarded to the arithmetic circuit 40 as the electrical resistivity $\rho_b$ of the blood and the electrical resistivity $\rho_p$ of the filtrate (plasma). The arithmetic circuit 40 calculates the hematocrit from the resistivities.

Here, since in formula (2) above, $K_2$ is the resistivity of the blood when hematocrit Ht=0, $K_2$ has to be the electrical resistivity $\rho_p$ of the plasma. That is, $K_2 = \rho_p$, then:

$$Ht = K_1 \ln \frac{\rho_b}{\rho_p} \tag{3}$$

Moreover, the relationship between the change $\Delta\rho_b$ ($\Omega$ cm) in the electrical resistivity of normal blood caused by the addition of NaCl thereto and the hematocrit Ht (%) can be expressed as:

$$\Delta\rho_b \propto e^{\frac{1}{K_3} Ht} \tag{4}$$

wherein it is known that $K_3$ equals about $\frac{1}{2}K_1$. Therefore, in a case where the NaCl concentration of the blood has come to vary from the normal value for a healthy person as a result of hemofiltration or hemodialysis, then the relationship among the electrical resistivity $\rho_b$ of the blood at 37° C., the electrical resistivity $\rho_p$ of the plasma and the hematocrit can be approximated as:

$$\rho_b + (54 - \rho_p) e^{\frac{2}{K_1} Ht} = 54 e^{\frac{1}{K_1} Ht}$$

or as:

$$e^{\frac{1}{K_1} Ht} = \frac{\rho_b}{54} + \frac{(54 - \rho_b)\left(e^{\frac{1}{K_1} Ht}\right)^2}{54} \tag{4}$$

Thus the fact that $K_1 \approx 47$ is established. The arithmetic circuit 40 uses this relationship to calculate the hematocrit from $\rho_b$ and $\rho_p$. More specifically, a shift circuit 88 first derives $(54 - \rho_p)$ from $\rho_b$ and $\rho_p$ in accordance with formula (4), whereafter a computation circuit consisting of an attenuator 90, an adder 92, a squarer 94, a multiplier 96 and an attenuator 98 derives $(1/K_1)$ Ht from $\rho_b$ of formula (4) and $(54 - \rho_p)$. Next, a logarithmic amplifier 100 calculates Ht.

Figure 6:
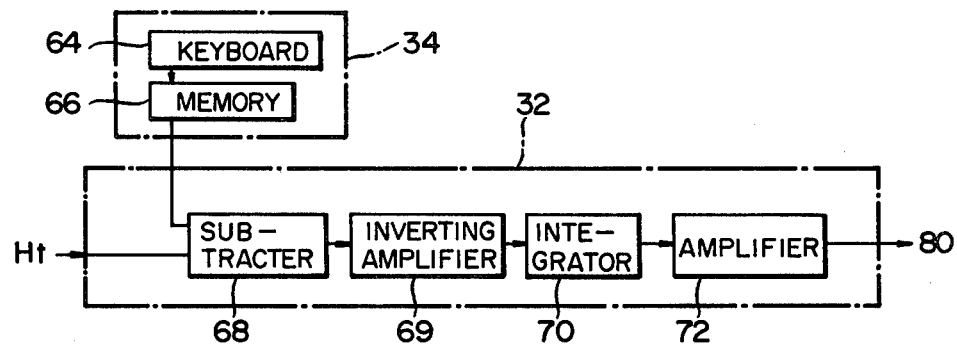
FIG. 6 is a block diagram of the control section used in the embodiment of FIG. 4.

Thus, in the manner just described, the hematocrit Ht is calculated taking into consideration the effect of changes in the electrolytic concentration resulting from hemofiltration and, using this hematocrit, the control section 14 carries out control as in the first embodiment, except that in this second embodiment the replacement fluid section 76 constituting a regulator for the circulating blood volume in the patient's body is controlled in accordance with a predetermined program. The control unit 32 of this second embodiment is shown in FIG. 6 and as will be noted it is the same as that in the first embodiment except that it is provided with an inverting amplifier 69 between the subtractor 68 and the integrator 70.

The operation of the second embodiment of the invention constructed as described above will now be explained in the following.

In this second embodiment, too, a program matched to the condition of the patient is loaded in the hematocrit memory prior to the start of hemofiltration, and when hemofiltration is begun, this program and the hematocrit Ht obtained by measurement of blood and ultrafiltrate resistivity are compared, and the supplying rate of replacement fluid is appropriately controlled accordingly.

That is to say, when the circulating blood volume in the patient's body falls appreciably and the hematocrit Ht rises to become larger than the programmed value, the replacement fluid injection rate is increased to increase the amount of blood in the patient's body. On the other hand, when circulating blood volume becomes greater than the programmed value, the feed of replacement fluid is reduced to remove the excessive body fluid accumulated in the patient, more effectively.

As described above, in this second embodiment, the circulating blood volume within the patient's body is controlled on the basis of the hematocrit Ht in a manner well matched to the condition of the particular patient being treated so that appropriate water removal can be carried out without giving rise to associated disorders and complications.

Figure 7:
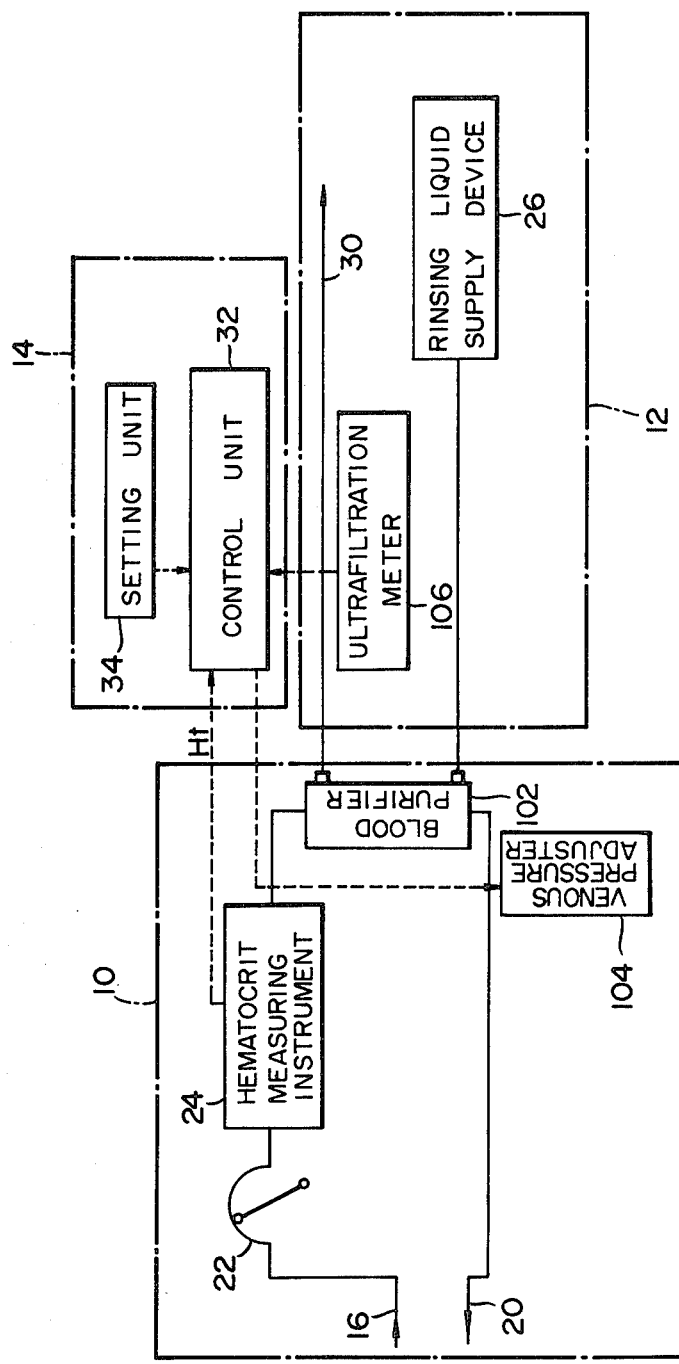
FIG. 7 is a block diagram of the third embodiment of the blood purification apparatus in accordance with this invention.

Third embodiment:

The third embodiment of the invention is shown in FIG. 7. As in the preceding two embodiments, this embodiment also carries out hemodialysis in a manner characterized by the fact that water removal is appropriately controlled on the basis of the continuous measurement of both the hematocrit and the amount of removed water.

As was explained in conjunction with the second embodiment, in order to measure the hematocrit with high accuracy in a case where the electrolytic concentration of the blood is changed by the blood purification process, it is necessary to measure the electrical resistivities of both the blood and the plasma. This third embodiment is similar to the first embodiment in that hemodialysis is carried out by supplying dialysate from the dialysate supply device 26 of the dialysate section 12 to a blood purifier 102 on the side thereof divided from the blood side by a semipermeable membrane. Therefore, in order to measure the electrical resistivity of the blood plasma, there is provided separately of the blood purifier 102 and within the hematocrit measuring instrument 24 a hemofilter for separating off a part of the plasma from the blood. This hemofilter provides the ultrafiltrate required for measuring the electrical resistivity of the blood plasma.

In this third embodiment, the circulating system 10 is provided in the return pipe 20 with a venous pressure adjuster 20 which regulates the pressure on the semipermeable membrane of the blood purifier 102 in accordance with a signal from the control section 14 and functions as a regulator for the circulating blood volume in the patient's body.

In this third embodiment, the hematocrit is measured in the circulating system 10 and, in addition, the amount of water removed is measured in the dialysate section 12. For the purpose of measuring the removed water, the dialysate section is provided with an ultrafiltration meter 106 which measures the amount of dialysate supplied to the blood purifier 102 on its inlet side and the amount of waste fluid issuing from the blood purifier on its outlet side. This arrangement makes it possible to determine the amount of ultrafiltrate from the difference between the amount of supplied dialysate and the amount of waste liquid, and the amount so determined is converted to a water removal quantity signal which is forwarded to the control unit 32 of the control section 14.

Figure 8:
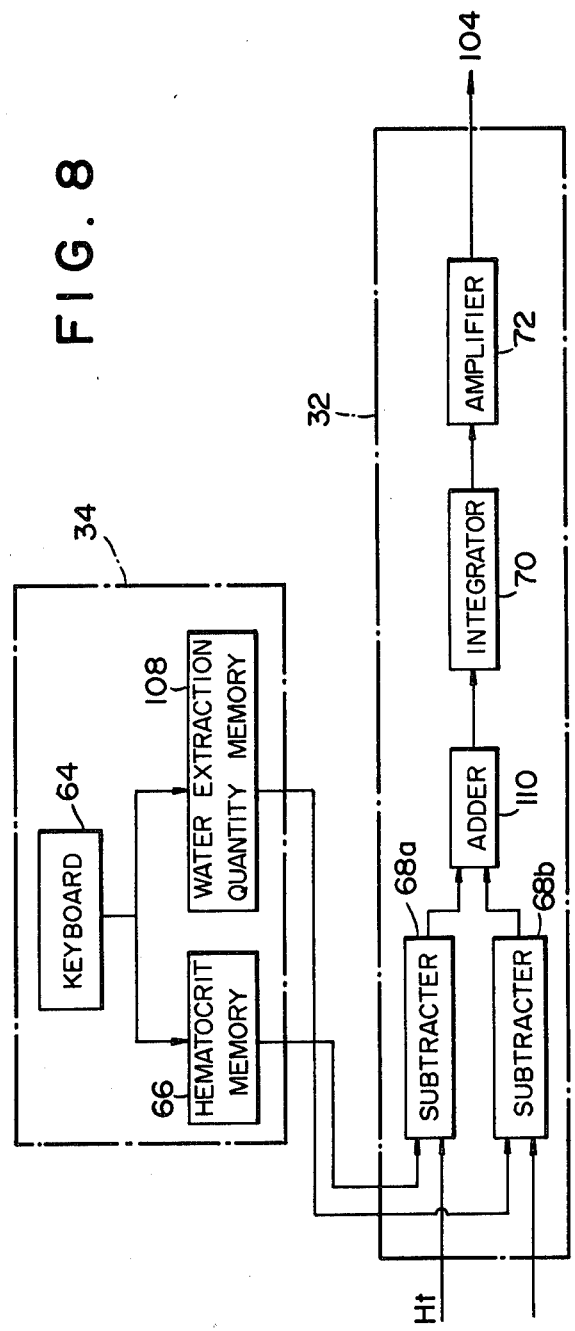
FIG. 8 is a block diagram of the control section used in the embodiment of FIG. 7.

FIG. 8 shows the structure of the control section 14 of the third embodiment. Separately of the hematocrit memory 66, the setting unit 34 is provided with a water removal quantity memory 108 in which there is stored a water removal quantity program matched to the preferred pattern of water removal for the patient during the process of blood purification. The hematocrit program and the water quantity removal program are supplied separately to the control unit 32.

The outputs from the memories 66,108 are fed to subtracters 66a, 66b, respectively, where they are subtracted from the hematocrit and the amount of ultrafiltrate (water removal quantity), both of which are measured continuously throughout the blood purification operation. The results of both of these subtractions are forwarded to an adder 110 where they are added and then forwarded to the integrator 70 and the amplifier 72. The output from the amplifier 72 is forwarded to the venous pressure adjuster 104 as a control signal.

In the control section 14 of the construction described above, when the values of the hematocrit and the amount of ultrafiltrate actually measured in the course of blood purification are smaller than the prescribed values, the venous pressure adjuster 104 is controlled to increase the venous pressure in the circulating system 10, thereby increasing the amount of ultrafiltration. On the other hand, when the measured values are larger than the prescribed values, the venous pressure is decreased to thereby reduce the amount of ultrafiltration.

Therefore, by means of this third embodiment, it is possible to carry out efficient water removal without excessive reduction of the circulating blood volume in the patient's body. Moreover, if during the blood purification process the measured value of the hematocrit should be larger than the prescribed value in spite of the fact that the measured value of ultrafiltration is smaller than the prescribed value, it is possible to freely determine whether the amount of ultrafiltration is to be increased or decreased for given degrees of difference between the respective measured and prescribed values. For this it is possible to appropriately weight the subtracters 68a, 68b in this embodiment in accordance with the importance placed on each of the hematocrit and the amount of ultrafiltration.

In the embodiments described above, although the hematocrit is applied to the control section without modification, it is also possible to apply it as its reciprocal or in some other mathematically modified form.

Again, though in the above-described embodiments the hematocrit is measured to provide a dependable standard for determining the circulating blood volume within the patient's body with high reliability, it is otherwise possible in accordance with this invention to derive the protein concentration of blood via the oncotic pressure measured using a semipermeable membrane and to use the changes in protein concentration to calculate the changes in the amount of circulating blood.

Here it should be noted that in determining the amount of circulating blood from this oncotic pressure, as it is necessary to measure minute differences in pressure across the semipermeable membrane, it is imperative to carry out strict quality control with respect to the semipermeable membrane properties.

Figure 9:
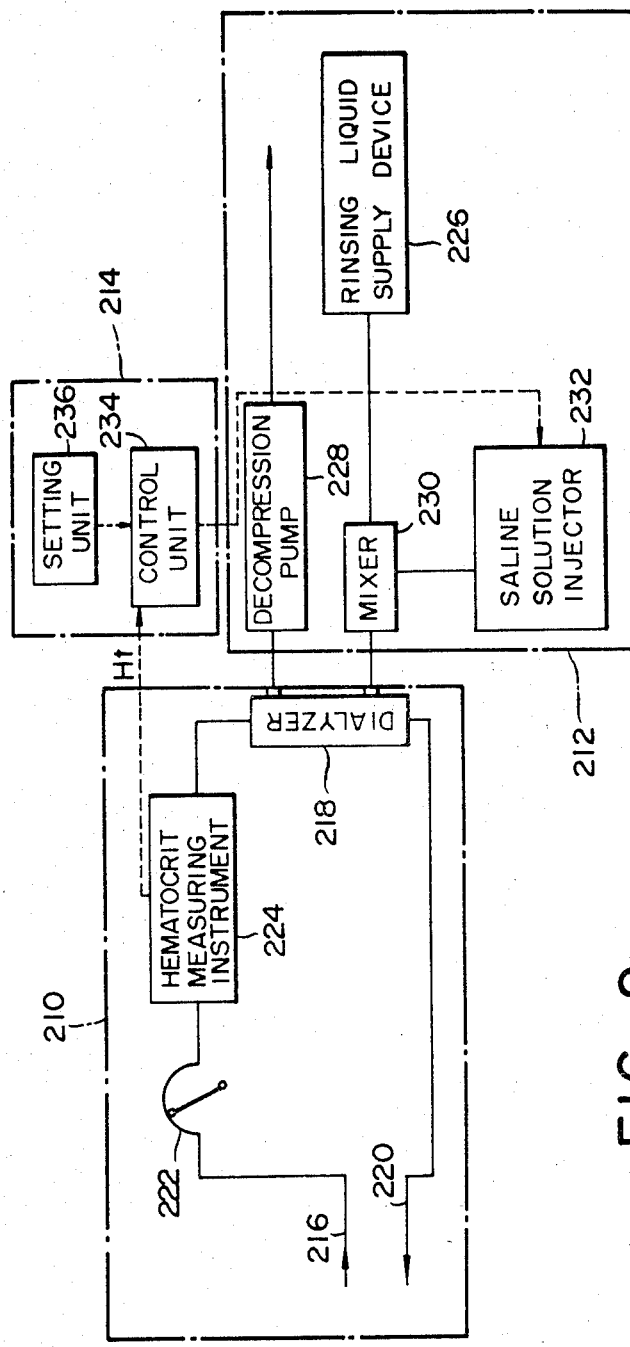
FIG. 9 is a block diagram of the fourth embodiment of the blood purification apparatus in accordance with this invention.

Fourth embodiment:

FIG. 9 shows the basic structure of the fourth embodiment of the invention, which is used in hemodialysis. This fourth embodiment includes a circulatory path 210 through which blood removed from the patient's body is circulated, a dialysate section 212 for supplying dialysate to the blood purifier in the circulatory path 210, and a control section 214 for controlling the circulating blood volume within the patient's body in response to the amount of blood detected, in the circulatory path 210, to be circulating within the patient's body, particularly in this embodiment, in response to the hematocrit value.

In the circulatory path 210, blood from the patient is fed via an inlet pipe 216 to a dialyzer 218 which purifies the blood by dialysis and ultrafiltration in cooperation with the dialysate section 212 and then returns the purified blood to the patient via a return pipe 20. During this process the blood is circulated by a circulation pump 22.

It is a feature of this invention that in order to carry out safe and efficient removal of waste products in a dialyzer such as that described above, there is provided a hematocrit measuring instrument 224 in the circulatory path 210. This hematocrit measuring instrument 224 continuously measures the electrical resistance of the blood to obtain the blood hematocrit, and the osmotic pressure of the blood plasma is regulated to maintain the circulating blood volume within the patient's body, which amount is inversely proportional to the hematocrit, in conformity with a predetermined program representing a pattern of variation in the circulating blood volume in the patient's body which is matched to the condition of the patient.

The dialysate section 212 is provided with a known dialysate supply device 226 which supplies dialysate to the dialyzer 218 and the outlet side of the dialyzer is connected with a decompression pump 228. Therefore, a negative pressure due mainly to the decompression produced by the decompression pump 228 is applied to the semipermeable membrane of the dialyzer 218 so that water and solutes with molecular weights of not more than 10,000 are ultrafiltered to the dialysate side of the semipermeable membrane.

Further, in the feed path for feeding dialysate from the dialysate supply device 226 to the dialyzer 218 there are provided a mixer 230 and a saline solution injector 232 which together constitute a regulation system for the circulating blood volume in the patient's body. The saline solution injector 232 supplies a controlled amount of a concentrated sodium chloride solution to the mixer 230 which mixes the dialysate and concentrated sodium chloride solution fed thereto and supplies the mixture to the dialyzer 218. In this embodiment, the injection rate of the saline solution injector 232 is varied by the control section 214 in accordance with the hematocrit. In this way, by appropriately controlling the sodium chloride concentration of the dialysate according to the condition of the particular patient undergoing blood purification, the circulating blood volume in the patient's body can be maintained at the prescribed level, thus enabling optimum blood purification without danger of causing associated disorders or complications.

The control section 214 consists of a control unit 234 for controlling the saline solution injector 232 on the basis of the measured value from the hematocrit measuring instrument 224 and a prescribed program, and a setting unit 236 for storing a program corresponding to the desired hematocrit variation pattern for the patient as determined from his medical record. The setting unit 236 includes a circulating blood memory wherein there is loaded a program representing the desired pattern of change in the circulating blood volume within the patient's body, this program being matched to the condition of the particular patient undergoing blood purification.

In this embodiment, as the hematocrit measuring instrument 224 there is used the instrument shown in FIG. 2. With a view to assuring the safety of the patient and avoiding the effect of polarization, a current of 25 KHz and 30 µA rms is supplied from the constant AC current source 54 and, moreover, the voltmeter 56 converts the AC voltage to a DC voltage which it forwards to the temperature compensator 38.

In accordance with this arrangement, the electrical resistivity value obtained from the resistivity measurement device 36 is compensated for temperature by the temperature compensator 38 according to the resistance of the thermistor 58. Taking into consideration that in the vicinity of body temperature the electrical resistivity of blood decreases about 2% per 1° C. increase in temperature, the temperature compensation is carried out so as to convert the measured resistivity to that at 37° C.

Next, the temperature-compensated resistivity value is forwarded to the arithmetic circuit 40 where it is used to calculate the hematocrit. The relationship between the resistivity $\rho_b$ (Ω cm) of blood in the vicinity of 25 KHz and the hematocrit Ht according to the centrifugation method can be expressed as:

$$\rho_b = K_2 e^{\frac{1}{K_1} Ht} \quad (1)$$

As, however, $K_1 \approx 47$ and $K_2 \approx 54$, the hematocrit Ht can be obtained as follows:

$$Ht = K_1 l_n \frac{\rho_b}{K_2} \quad (2)$$

The arithmetic circuit 40 is provided with an attenuator 60 and a logarithmic amplifier 62 for calculating Ht in accordance with the formula (2).

Figure 10:
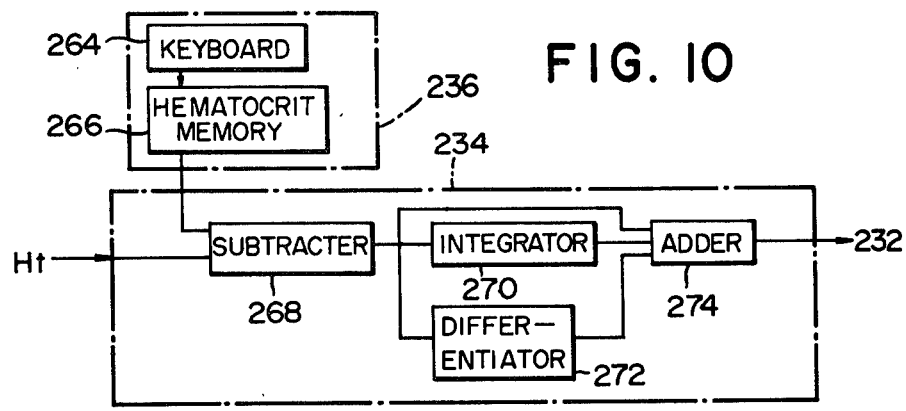
FIG. 10 is a block diagram of the control section used in the embodiment of FIG. 9.

It is a feature of this invention that the hematocrit calculated from the electrical resistivity of the blood in this way is used by the control section 214 to control the circulating blood volume in the patient's body. A preferred embodiment of the control section 214 is shown in FIG. 10.

In this embodiment the setting unit 236 stores the information obtained from patient's medical records on the preferable pattern of variation in the circulating blood volume in the patient's body during dialysis as the pattern of hematocrit variation. It thus includes a keyboard 264 for imputting the hematocrit pattern program and a memory for storing information on the circulating blood volume in the patient's body, namely in this embodiment, hematocrit memory 266.

The control unit 234 is arranged to control the saline solution injector 232 of the dialysate section 212 on the basis of the program stored in the hematocrit memory 266 and the measured value from the hematocrit measuring instrument 224. It therefore comprises a subtractor 268 for obtaining the difference between the hematocrit value according to the program stored in the hematocrit memory 266 and the measured hematocrit Ht obtained from the hematocrit measuring instrument 224 during dialysis, an integrator 270 for integrating this difference, a differentiator 272 for differentiating the same difference, a subtractor 268, and an adder 274 which weights and adds the outputs of the integrator 270 and the differentiator 272 to produce a control signal.

In this invention, in the case where the hematocrit Ht is smaller than the value set by the program, the injection rate of the injector 232 is gradually decreased and, on the contrary, when the hematocrit Ht is larger than the set value, the injection rate of the injector 232 is gradually increased, whereby the circulating blood volume in the patient's body is maintained at the prescribed level by regulating the osmotic pressure of the blood plasma.

The operation of the fourth embodiment of the invention constructed as described above will now be explained in the following.

Prior to the start of hemodialysis, there is loaded in setting unit 234 a program reflecting the optimum pattern of hematocrit variation for the patient prepared on the basis of any increase in the patient's weight, his blood pressure and other aspects of his medical record between the completion of the preceding dialysis and the beginning of the current one. Following this, hemodialysis is conducted in the known manner.

In the present invention, the hematocrit is continuously measured during hemodialysis and, using the measured value, the control section 234 controls the purification operation in accordance with the aforementioned program.

In the course of hemodialysis, a desired level of ultrafiltration is generally carried out under the mechanical pressure exerted on the semipermeable membrane of the dialyzer 218 from the side of the circulatory path 210 and by the decompression pump 228, and under the osmotic pressure between the blood and the dialysate. In other words, by maintaining the pressure on the dialysate side at a lower level, water contained in the blood is ultrafiltered through the semipermeable membrane to the dialysate side. At this time, the amount of ultrafiltered water per unit time is not equal to the amount of water passing into the blood from the body tissues of the patient and this results in changes in the circulating blood volume within the patient's body during hemodialysis. Normally, about 1-3 l of water is removed during a single hemodialysis (4-6 hours) and this causes a decrease in the circulating blood volume within the patient's body. It is a feature of this invention that in the course of hemodialysis the circulating blood volume within the patient's body is controlled so as to be constantly maintained at a predetermined programmed value. To accomplish this, attention has been given to the fact that the volume of the blood cells remains constant during hemodialysis (since they cannot pass through the semipermeable membrane) so that the circulating blood volume within the patient's body is inversely proportional to the hematocrit. Therefore, the circulating blood volume in the patient's body can be maintained constant by controlling the saline solution injector 232 so as to maintain the hematocrit, as measured, at the desired programmed value.

Therefore, in the fourth embodiment, when the passage of water from the interior of the cells and the tissue interstices into the blood vessels decreases and the amount of circulating blood drops quickly as the result of water removal, since at this time the hematocrit will rise above the programmed value, the amount of saline solution injected by the injector 232 is increased to raise the osmotic pressure of the plasma and prevent decrease in the amount of circulating blood. A similar type of control is also applied in the reverse case. As a consequence, by carrying out control in accordance with a predetermined pattern in this way it becomes possible to carry out removal of waste products in a manner well suited to the patient's condition.

Figure 11:
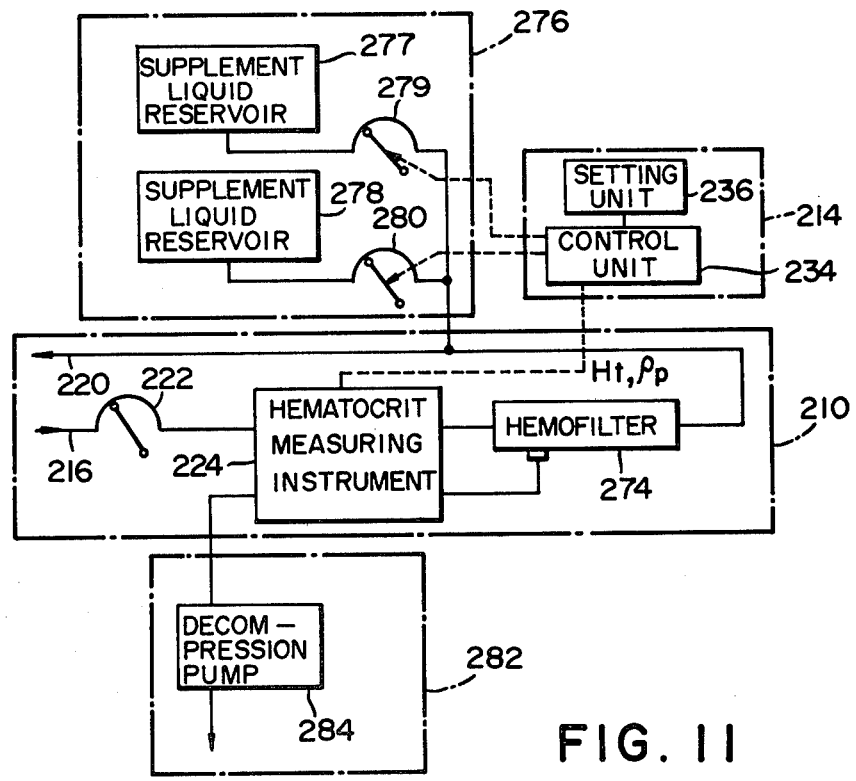
FIG. 11 is a block diagram of the fifth embodiment of the blood purification apparatus in accordance with this invention.

Fifth embodiment:

FIG. 11 shows a fifth embodiment of the blood purification apparatus according to this invention. Parts identical with those of the first embodiment are indicated by like reference numerals and explanation thereof is omitted.

Similarly to the fourth embodiment, the fifth embodiment is also characterized by the fact that optimum purification is carried out by comparing the circulating blood volume in the patient's body during the purification operation with the patient's program while at the same time comparing the osmotic pressure of the blood plasma with the prescribed value.

Differently from the case of the fourth embodiment, however, in this fifth embodiment purification is carried out by hemofiltration.

A part of the components of the blood plasma including waste products is ultrafiltered from the blood by a hemofilter 274 and a decompression pump 284 provided in a waste fluid section 282 connected in communication with the waste filtrate side of the hemofilter 274. During this hemofiltration, replacement fluid is supplied to the circulatory path 210 from a replacement fluid section 276. The purified blood is returned to the patient.

In this embodiment, the replacement fluid section 276 comprises a first replacement fluid reservoir 277 containing replacement fluid of a sodium concentration equal to or slightly lower than that used in the ordinary hemofiltration method (between 135 and 140 mEq/l, for example), a first feed pump 279 for supplying this replacement fluid to the circulatory path 210, a second replacement fluid reservoir 288 containing a concentrated sodium chloride (NaCl) solution, and a second feed pump 280 for supplying this replacement fluid (concentrated NaCl solution) to the circulatory path 210, the first feed pump 279 of the replacement fluid section 276 constituting a water removal regulator, the second feed pump 280 constituting a plasma osmotic pressure regulator, and said water removal regulator and plasma osmotic pressure regulator together constituting a regulator for the circulating blood volume in the patient's body. By varying the operating speed (rpm) of the feed pumps 279, 280 under the control of a control signal from the control section 214, the amount and concentration of the replacement fluid supplied to the circulatory path 210 is regulated so as to control the amount and NaCl concentration of the blood circulating within the patient's body.

In this embodiment, the hematocrit of the blood in the circulatory path 210 is measured and the measured value is used to control the replacement fluid section 276 which regulates the circulating blood volume in the patient's body. In this embodiment, since a large quantity of replacement fluid having a different electrolytic concentration from the body fluids is injected into the patient's body from the replacement fluid section 276, a change occurs in the electrolytic concentration and electrical resistivity of the blood plasma. Under these circumstances, a hematocrit Ht calculated from only the electrical resistivity in accordance with formula (2) will involve an element of error. Therefore, in this embodiment, the hematocrit Ht is calculated in accordance with formulas (5) and (6) from both the electrical resistivity $\rho_b$ ($\Omega$ cm) of the blood and the electrical resistivity $\rho_s$ ($\Omega$ cm) of the waste filtrate liquid which constitutes one part of the blood plasma.

$$\rho_p = K_2 \cdot \rho_s \qquad (5)$$

$$e^{\frac{1}{K_1} Ht} = \frac{\rho_b}{54} + \frac{(54 - \rho_p)\left(e^{\frac{1}{K_1} Ht}\right)^2}{54} \qquad (6)$$

In calculating the electrical resistivity $\rho_p$ of the plasma from the electrical resistivity $\rho_s$ of the waste filtrate liquid, although $K_2$ may vary somewhat with the plasma protein concentration, the best results are obtained by assuming $K_2 = 1.05$ and $K_1 = 47$.

Figure 12:
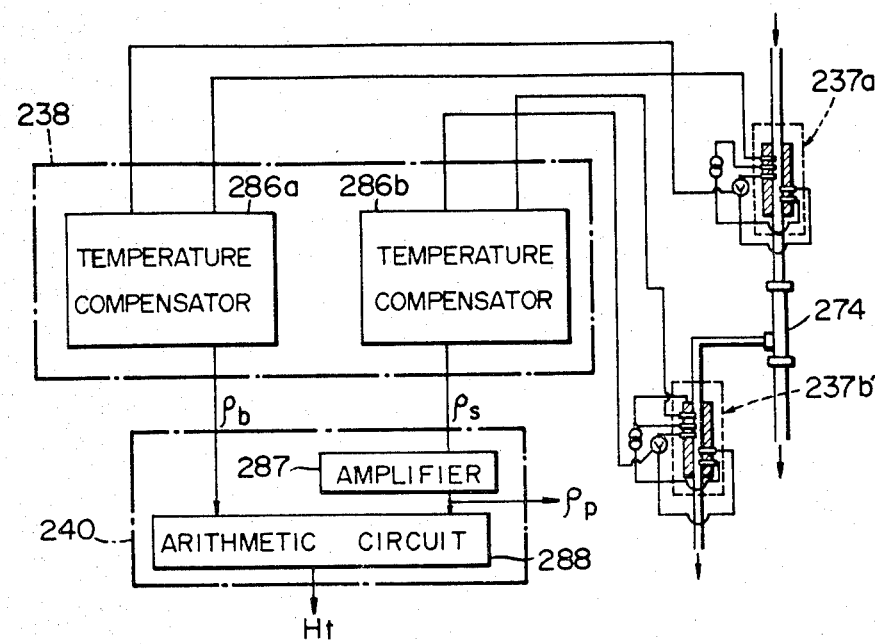
FIG. 12 is an explanatory view of the hematocrit measuring instrument used in the embodiment of FIG. 11.

The structure of the hematocrit measuring instrument 224 is shown in FIG. 12, wherein it will be noted that in the circulatory path 210 the waste fluid from the hemofilter 274 is supplied to the hematocrit measuring instrument 224.

As shown in FIG. 12, resistivity measurement devices 237a and 237b are provided one on the blood inlet side and one on the waste fluid outlet side of the hemofilter 274. These resistivity measurement devices are of the same structure as that shown in FIG. 2. The electrical resistivity measurements from these devices 237a, 237b are forwarded to temperature compensators 286a, 286b where they are converted to the corresponding values for the blood at 37° C. and the compensated values are forwarded to the arithmetic circuit 40 as the electrical resistivity $\rho_b$ of the blood and the electrical resistivity $\rho_s$ of the filtrate. The arithmetic circuit 40 calculates the hematocrit from the resistivities.

The hematocrit Ht is calculated from $\rho_b$ and $\rho_s$ in accordance with the formulas (5) and (6). More specifically, $\rho_p$ is obtained from $\rho_s$ by an amplifier 287 having a gain of $K_2$, whereafter an arithmetic circuit 288 calculates the hematocrit Ht in accordance with the formula (6).

In this embodiment, the NaCl concentration of the replacement fluid is regulated to control the NaCl concentration of the plasma (i.e. the osmotic pressure of the plasma) and in this way the passage of intracellular water to the exterior of the cells is regulated to maintain an appropriate distribution of body fluids. To prevent an excessive or unnecessary rise in the NaCl concentration of the blood plasma during this process, this embodiment monitors the NaCl concentration of the blood plasma and on the basis of the monitored concentration controls the NaCl concentration of the replacement fluid. Most of the NaCl in the plasma is divided into Na ions and Cl ions and it is these which account for the major part of the plasma electrolyte. Thus it is possible to determine the NaCl concentration of the plasma from the electrical resistivity $\rho_b$ of the plasma. This embodiment is thus provided with a plasma osmotic pressure measurement section composed of the hematocrit measuring instrument 224, the filtrate resistivity measurement device 36, the temperature compensator 286b and an amplifier 287.

Thus, there is obtained both the variation in the electrical resistivity of the plasma caused by the process of hemofiltration and a hematocrit which reflects the effect of this variation and on the basis of this electrical resistivity $\rho_b$ of the plasma and the hematocrit, the control section 214 controls the replacement fluid section 276 which in this embodiment constitutes the regulator for the circulating blood volume in the patient's body.

Figure 13:
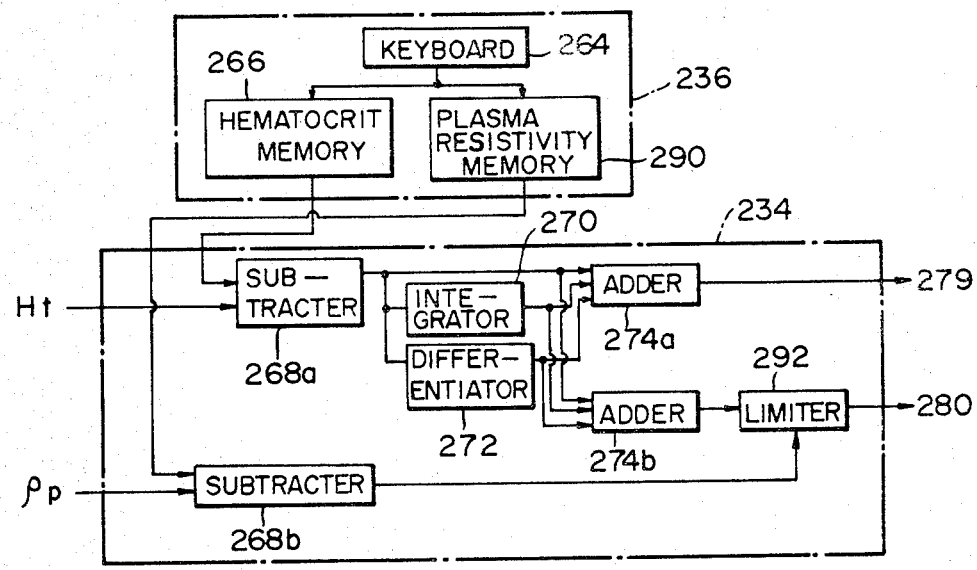
FIG. 13 is a block diagram of the control section used in the embodiment of FIG. 11.

The control section of the fifth embodiment is shown in FIG. 13. In addition to the hematocrit memory 266, the setting unit 236 is provided with a plasma osmotic pressure memory which stores the upper limit of the plasma NaCl concentration in the form of the electric resistivity $\rho_p$ (as $\rho_p$ falls with rising NaCl concentration, the value stored is the lower limit of $\rho_p$). In the present embodiment, the role of this memory is played by a plasma resistivity memory 290. The hematocrit program and the prescribed value of the plasma resistivity are thus separately supplied to the control unit 234.

As in the fourth embodiment, the control unit 234 is provided with the subtracter 268a, the integrator 272, and the adders 274a and 274b which, on the basis of the value received from the memory 266 and the hematocrit Ht which is continuously measured during the course of blood purification, produce control signals for the first and second feed pumps 279, 280, and is provided additionally with a limiter 292 which limits or decreases the signal output to the second feed pump 280 from the adder 274b when the difference calculated by the subtracter 268b between the prescribed value from the plasma resistivity memory 290 and the measured value of the plasma resistivity becomes zero or negative. Thus, as described above, the regulator for the circulating blood volume in the patient's body in this fifth embodiment is comprised of a water removal regulator constituted by the first feed pump 279 for supplying to the circulatory path 210 replacement fluid of an osmotic pressure equal to or somewhat lower than that normally used, and a plasma osmotic pressure regulator constituted by the second feed pump 280 for supplying high osmotic pressure supplement liquid. These two regulators receive separate control signals from the separately provided adder 274a and adder 274b, each of which adds to the deviation signal from the subtracter 268a both the differentiated value and the integrated value of this deviation signal, in an appropriately weighted relationship.

The operation of the fifth embodiment of the invention constructed as described above will now be explained in the following.

Prior to the start of hemofiltration, a program for the pattern of change in the circulating blood volume in the patient's body best matched to the patient's condition is loaded in the hematocrit memory 266 and the prescribed value for the plasma osmotic pressure is loaded in the plasma resistivity memory 290. With the start of hemofiltration, the hematocrit Ht measured from the patient's blood and corresponding to the circulating blood volume within the patient's body and the plasma resistivity $\rho_p$ measured from the ultrafiltrate and corresponding to the osmotic pressure of the blood plasma are compared with the aforesaid program and prescribed value, respectively, and on the basis of this comparison the supply of replacement fluid is appropriately controlled to maintain the circulating blood volume within the patient's body at the prescribed level.

More specifically, when the amount of water removal from the patient is insufficient, the hematocrit Ht will fall below the prescribed value, whereupon the output from the adder 274a causes a reduction in the injection rate of the first feed pump 279 thus increasing the amount of water removal. At the same time, the output from the adder 274b causes a reduction in the injection rate of the second feed pump 280, thereby lowering the NaCl concentration of the replacement fluid. In this way, the removal of excess water from the patient's body is effectively carried out while at the same time preventing any rise in the osmotic pressure of the patient's plasma. On the other hand, when the circulating blood volume in the patient's body is smaller than the programmed value, the injection rates of the first and second feed pumps 279, 280 are increased to reduce the amount of water while at the same time increasing the NaCl concentration of the replacement liquid, in this way promoting the passage of water out of the cells and increasing the amount of circulating blood.

Also in this embodiment, when, in the course of the above described control, the osmotic pressure of the patient's plasma is raised by increasing the output of the second feed pump 280, since this causes the plasma resistivity $\rho_p$ to fall below the prescribed value, the injection rate of the second feed pump 280 will be restricted so that the plasma osmotic pressure will not become excessively high.

Thus, since this fifth embodiment prevents both excessive decreases in the circulating blood volume in the patient's body and excessive increases in the plasma osmotic pressure, it makes it possible to carry out well-balanced removal of waste products from the blood without giving rise to associated disorders and complications.

Figure 14:
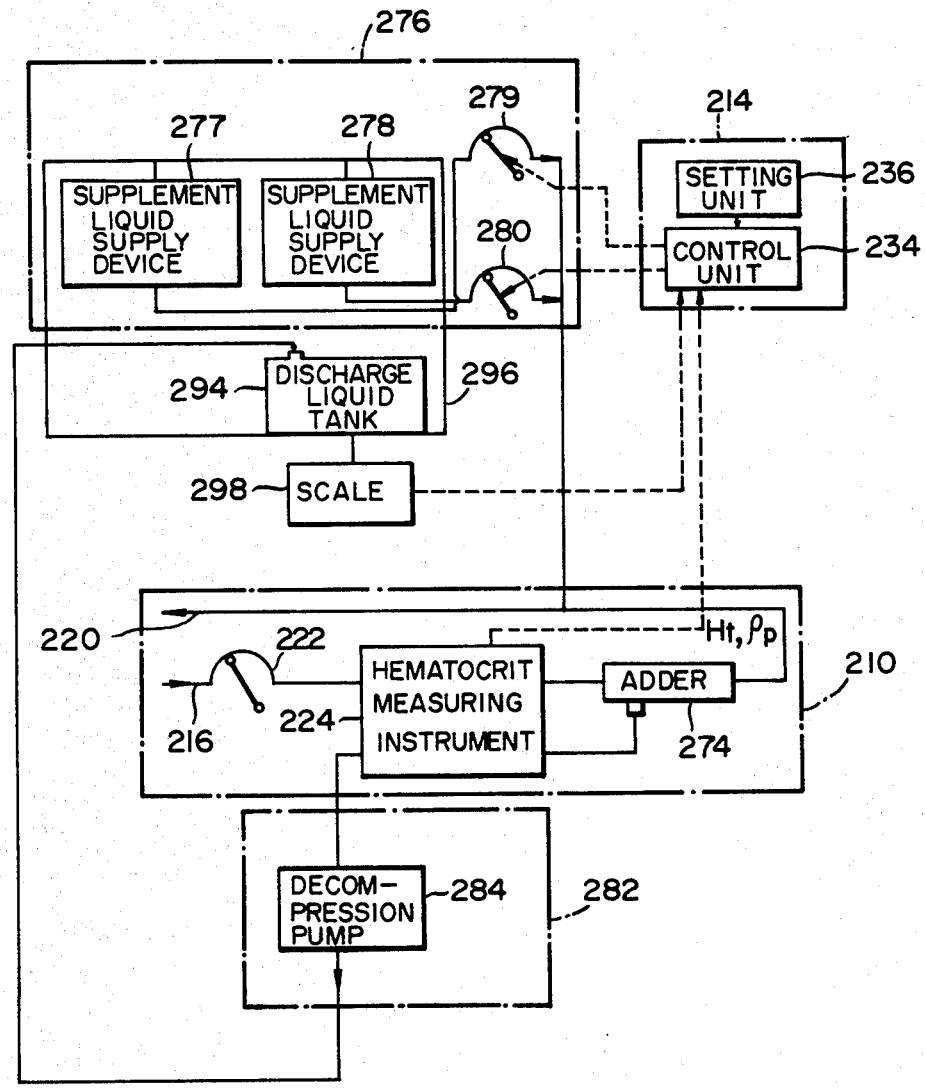
FIG. 14 is a block diagram of the sixth embodiment of the blood purification apparatus in accordance with this invention.

Sixth embodiment:

FIG. 14 shows the sixth embodiment of the invention. Parts identical with those of the fifth embodiment are indicated by like reference numerals and explanation thereof is omitted.

Similarly to the fifth embodiment, the sixth embodiment also carries out appropriate blood purification control on the basis of three factors: control of the hematocrit, control of plasma osmotic pressure and continuous measurement of water removal. In order to measure water removal this embodiment is provided with a discharge liquid tank 294 for storing the ultrafiltrate issuing from a waste liquid section 282, and the discharge liquid tank 294 and the replacement liquid reservoirs 277,278 of the replacement liquid section 276 are all integrally fixed on a table 296. The weight of the table 296 and the members thereon, as well as any change therein, is measured by a scale 298. Therefore, this scale measures the difference between the amount of waste liquid ultrafiltered from the patient's blood and the amount of replacement liquid added to the patient's blood, and the measured value is forwarded from the scale 298 to the control section 214 as a water removal quantity signal.

Figure 15:
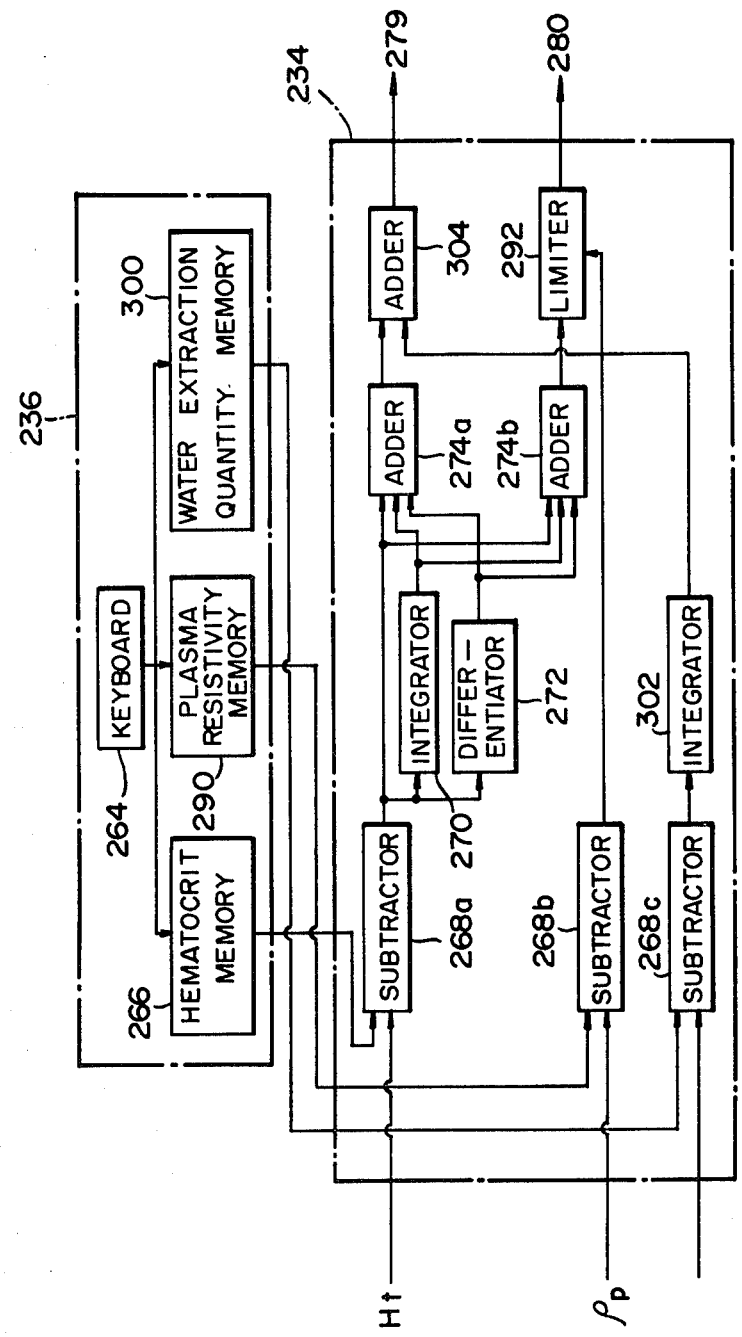
FIG. 15 is a block diagram of the control section used in the embodiment of FIG. 14.

The construction of the control section 214 of the sixth embodiment is shown in FIG. 15. In addition to the hematocrit memory 266 and the plasma resistivity memory 290, the setting unit 236 is provided with a water removal quantity memory 300 which stores a program for the best pattern of water removal for the patient during blood purification based on his medical records. The hematocrit program, the prescribed value of the plasma resistivity and the water removal program are thus separately supplied to the control unit 234.

In addition to those components of the control unit of the fifth embodiment, the control unit 234 of the sixth embodiment is provided with a subtractor 268c which subtracts the output of the water removal quantity memory from the water removal quantity continuously measured by the scale 298 during blood purification, an integrator 302 for integrating the output of the subtractor 268c, and an adder 304 which produces a control signal for the first feed pump of the water removal regulator by adding the output of the integrator 302 and the adder 274a in a weighted relationship appropriate for the particular patient whose blood is being purified.

In the control section 214 of the sixth embodiment constructed as described above, when during blood purification the measured values of the hematocrit and the water removal quantity are larger than the prescribed values, the injection rate of the first feed pump 279 is increased and, on the contrary, when they are smaller, the injection rate is lowered. Again, when the measured water removal quantity is smaller than the prescribed value but the measured hematocrit is larger than the prescribed value, or vice versa, the injection rate of the replacement liquid can be increased or decreased as desired by controlling the injection rate of the replacement liquid on the basis of the differences between the respective measured and prescribed values. At this time, the importance placed on each of the hematocrit and the water removal quantity can be reflected by properly weighting the outputs of the adder 274a and the integrator 302 according to the condition of the patient when they are added in the adder 304.

Further, control by the plasma osmotic pressure regulator on the basis of the hematocrit and the electrical resistivity of the plasma can be conducted in the same way as in the fifth embodiment.

Thus in accordance with the sixth embodiment, water removal can be carried out while maintaining an appropriate circulating blood volume within the patient's body during blood purification, and, in a case where it is impossible to meet both of the above-mentioned requirements because a large amount of waste products have accumulated in the patient's body, it is possible, by employing a prescribed degree of weighting, to carry out the removal of waste products from the blood while maintaining an appropriate balance between the two.

Other variations of the invention:

In the fourth to sixth embodiments described above, the measurement of the electrical resistivity of the blood is conducted by measurement cells connected to and in communication with an extracorporeal circulation system. The invention is not limited to this arrangement, however, and it is possible, for example, to conduct this measurement using electrodes located within an air chamber of the known type which is ordinarily provided within the extracorporeal circulation system for removing bubbles but which, for brevity of explanation, was not referred to in the preceding description. In this case, the electrodes can be located near the bottom of the air chamber or at some other portion thereof where they are free from the above-described effect of blood flow.

Although in the fourth to sixth embodiments the hematocrit is inputted to the control section in its unaltered form, it is also possible to use instead its reciprocal or some other mathematically modified form thereof.

In the fourth to sixth embodiments, in order to control the amount of blood flowing within the patient's body with high reliability, hematocrit measurement is used as a dependable means for determining the amount of circulating blood. In this invention, however, it is also possible to derive the protein concentration of the blood via the oncotic pressure measured using a semipermeable membrane and to use the changes in the protein concentration to calculate the changes in the amount of circulating blood.

Here is should be noted that in determining the amount of circulating blood from this oncotic pressure, as it is necessary to measure minute differences in pressure across the semipermeable membrane (30–35 mmHg), it is imperative to carry out strict quality control with respect to the properties of the semipermeable membrane.

Nor is the invention limited to the arrangement used in the fourth to sixth embodiments wherein the regulation is realized by controlling the amount of concentrated NaCl solution injection so as to control the NaCl concentration of the replacement liquid. Instead it is possible, for example, to control the injection ratios of two types of replacement liquids, one having a sodium concentration at the upper limit (e.g. 180 mEeq/l) and the other having a sodium concentration at the lower limit (e.g. 135 mEq/l). Also for changing the plasma osmotic pressure, it is possible to use other substances than sodium such as mannitol, glycerol, albumin etc. In the case of using one of these substances, however, it is necessary to use as the means for measuring the plasma osmotic pressure one that is capable of accurately measuring changes in the concentration of the substance and also to use a means for measuring the amount of circulating blood which is not affected by the substance concerned. For example, in the case of using albumin for the control of the plasma osmotic pressure, it is necessary to use a hematocrit measuring instrument or the like for the measurement of the amount of circulating blood.

In the fourth embodiment, the water removal regulator for the circulating blood volume in the patient's body regulates the pressure (negative pressure) on the dialysate side of the blood purifier (dialyzer) in order to vary the rate of ultrafiltration by the blood purifier. The invention is not limited to this arrangement, however, and instead, the rate of ultrafiltration can be varied, for example, by regulating the pressure (positive pressure) applied to the blood side of the blood purifier.

Effect of the invention:

As has been explained in the foregoing, in accordance with the present invention, the circulating blood volume within the patient's body is continuously measured during the blood purification process so that it is possible to automatically control the rate of water removal in accordance with a prescribed program matched to the patient concerned. Therefore, effective water removal can be carried out while maintaining the circulating blood volume within the patient's body at the optimum level.

Further, in accordance with the present invention, the circulating blood volume within the patient's body, the osmotic pressure of the plasma and the quantity of water removal are measured during the blood purification process so that the osmotic pressure of the plasma and the rate of water removal can be automatically controlled in accordance with a specified program or value matched to the patient under treatment so that it is possible to carry out well-balanced removal of waste products from the blood while maintaining the circulating blood volume within the patient's body at an appropriate level.

We claim:

1. A blood purification apparatus comprising: an extracorporeal circulation system, a blood purifier provided in said system for purifying blood by dialysis or filtration through a semipermeable membrane,
   a circulating blood volume measuring instrument connected to said extracorporeal circulation system for measuring changes in the circulating blood volume within a patient's body,
   a control section connected to said circulating blood volume measuring instrument, comprising a memory for storing a program for a pattern of changes in the circulating blood volume during blood purification, said program being matched to the condition of the patient, and
   a regulator connected to said extracorporeal circulation system and said control section, for controlling the circulating blood volume, said regulator being controlled by said control section on the basis of the circulating blood volume measured during blood purification and the programmed amount, whereby optimum blood purification is carried out while maintaining the circulating blood volume at a prescribed level.

2. An apparatus according to claim 1, further comprising a water removal quantity measurement device for measuring the amount of water removed from the patient's body connected to said control section, wherein said control section further comprises a water removal quantity memory for storing a water removal program and controls said regulator on the basis of a comparison of the circulating blood volume measured during blood purification and the measured quantity of removed water with programmed values.

3. An apparatus according to claim 1 wherein said regulator comprises a total body fluid volume change regulator.

4. An apparatus according to claim 2, wherein said regulator comprises a total body fluid volume change regulator.

5. An apparatus according to claim 1, wherein said regulator comprises a plasma osmotic pressure regulator.

6. An apparatus according to claim 5, further comprising a plasma osmotic pressure measurement device for substantially measuring the osmotic pressure of the plasma of the patient, connected to said extracorporeal circulation system, and said control section further comprises a plasma osmotic pressure memory for storing a prescribed value of plasma osmotic pressure and controls said regulator on the basis of a comparison of the circulating blood volume measured during purification with the programmed amount and of the measured plasma osmotic pressure with the prescribed value.

7. An apparatus according to claim 5, further comprising a water removal quantity measurement device for measuring the amount of water removed from the patient's body, wherein said control section further comprises a water removal quantity memory for storing a water removal program, and controls said regulator on the basis of a comparison of the circulating blood volume measured during blood purification with the programmed amount, of the measured plasma osmotic pressure with the prescribed value, and of the measured amount of removed water with the programmed amount.

8. An apparatus according to claim 5, wherein said plasma osmotic pressure regulator comprises a means for controlling the infusing rate of osmolal solution to control the plasma ocmotic pressure.

9. An apparatus according to claim 5, wherein said plasma osmotic pressure regulator comprises a means for varying the electrolytic concentration of plasma.

10. An apparatus according to claim 6, wherein said plasma osmotic pressure mmeasurement device comprises a means for measuring the electrolytic concentration of the plasma.

11. An apparatus according to claim 10, wherein said plasma osmotic pressure measurement device comprises at least one ion electrode for measuring the concentration of a specific ion in the plasma.

12. An apparatus according to claim 10, wherein said plasma osmotic pressure measurement device comprises a means for measuring the electrolytic concentration of the plasma from its electrical resistivity.

13. An apparatus according to claim 3, wherein said total body fluid volume change regulator comprises a water removal regulator.

14. An apparatus according to claim 1, wherein said circulating blood volume measuring instrument is a hematocrit measuring instrument which detects changes in the circulating blood volume as changes in the hematocrit.

15. An apparatus according to claim 14, wherein said hematocrit measuring instrument comprises a resistivity measurement device for measuring the electrical resistivity of the blood in said extracorporeal circulation system, a temperature compensator for compensating the measured resistivity for temperature, and an arithmetic circuit for calculating the hematocrit from the electrical resistivity.

16. An apparatus according to claim 14, wherein said hematocrit measuring instrument comprises a resistivity measuring device for measuring the electrical resistivity of the blood in said extracorporeal circulation system, a temperature compensator for compensating the measured resistivity for temperature and an arithmetic circuit for calculating the hematocrit from the electrical resistivity, and the resistivity measurement device has a measurement cell including at least one pair of electrodes provided in an insulative pipe communicating with said extracorporeal circulation system at positions symmetrically opposed with respect to the axis of thee insulative pipe and separated from each other by a prescribed distance in the axial direction of said insulative pipe.

17. An apparatus according to claim 14, wherein said hematocrit measuring instrument comprises a resistivity measuring device for measuring the electrical resistivity of the blood in said extracorporeal circulation system and electrical resistivity of the plasma component of the blood, temperature compensators for compensating the measured resistivity for temperature and an arithmetic circuit for calculating the hematocrit from the electrical resistivity, and the hematocrit is calculated from both the electrical resistivity of the blood and the electrical resistivity of the plasma component.

18. An apparatus according to claim 16, wherein said resistivity measurement device is further provided with a measurement cell for measuring the electrical resistivity of the plasma component of the blood, and the hematocrit is calculated from both the electrical resistivity of the blood and the electrical resistivity of the plasma component.

19. An apparatus according to claim 17, wherein a filter is provided for ultrafiltrating a portion of the plasma from said extracorporeal circulation system and the measurement cell for measuring the electrical resistivity of the plasma component is provided in a waste filtrate path of said filter.

20. An apparatus according to claim 18, wherein a filter is provided for ultrafiltrating a portion of the plasma from said extracorporeal circulation system and the measurement cell for measuring the electrical resistivity of the plasma component is provided in a waste filtrate path of said filter.

21. An apparatus according to claim 20, further comprising:
a water removal quantity measurement device for measuring the amount of water removed from the patient's body, connected to said control section, and
a plasma osmotic pressure measurement device for substantially measuring the osmotic pressure of the plasma of the patient, connected to said extracorporeal circulation system and said control section, said resistivity measurement device having a measurement cell including two pairs of electrodes,
wherein said regulator comprises a total body fluid volume change regulator and a plasma osmotic pressure regulator, and
said control section further comprises a water removal quantity memory for storing a water removal program, and a plasma osmotic pressure memory for storing a prescribed value of plasma osmotic pressure and controls said regulator on the basis of a comparison of the circulating blood volume measured during blood purification with the programmed amount, of the measured plasma osmotic pressure with the prescribed value, and of the measured amount of removed water with the programmed amount.

22. An apparatus according to claim 1, wherein said regulator comprises a total body fluid volume change regulator and a plasma osmotic pressure regulator.

23. An apparatus according to claim 22, further comprising a plasma osmotic pressure measurement device for substantially measuring the osmotic pressure of the plasma of the patient, connected to said extracorporeal circulation system, and said control section further comprises a plasma osmotic pressure memory for storing a prescribed value of plasma osmotic pressure and controls said regulator on the basis of a comparison of the circulating blood volume measured during blood purification with the programmed amount and of the measured plasma osmotic pressure with the prescribed value.

24. An apparatus according to claim 3, wherein said total body fluid volume change regulator comprises a means for infusing a replacement fluid into said extracorporeal circulation system.

25. An apparatus according to claim 16, wherein said resistivity measurement device has a measurement cell including two pairs of electrodes.

* * * * *